US009556913B2

(12) United States Patent
Bongaerts et al.

(10) Patent No.: US 9,556,913 B2
(45) Date of Patent: Jan. 31, 2017

(54) CAPACITANCE MEASUREMENT IN A BEARING HOUSING

(71) Applicants: Jeroen Bongaerts, GK Hilversum (NL); Florin Tatar, GE Delft (NL)

(72) Inventors: Jeroen Bongaerts, GK Hilversum (NL); Florin Tatar, GE Delft (NL)

(73) Assignee: AKTIEBOLAGET SKF, Gothenburg (SE)

( * ) Notice: Subject to any disclaimer, the term of this patent is extended or adjusted under 35 U.S.C. 154(b) by 0 days.

(21) Appl. No.: 15/082,371

(22) Filed: Mar. 28, 2016

(65) Prior Publication Data

US 2016/0281787 A1 Sep. 29, 2016

(30) Foreign Application Priority Data

Mar. 27, 2015 (GB) .................................... 1505264.0

(51) Int. Cl.
*F16C 41/00* (2006.01)
*G01N 33/28* (2006.01)
*G01N 27/22* (2006.01)
*F16C 33/66* (2006.01)

(52) U.S. Cl.
CPC ........... *F16C 41/00* (2013.01); *F16C 33/6603* (2013.01); *F16C 33/6622* (2013.01); *G01N 27/22* (2013.01); *G01N 33/2847* (2013.01); *G01N 33/2888* (2013.01); *F16C 2233/00* (2013.01)

(58) Field of Classification Search
CPC ........................ F16C 41/007; F16C 2233/00
See application file for complete search history.

(56) References Cited

U.S. PATENT DOCUMENTS 6,196,057 B1 * 3/2001 Discenzo ................ F16C 19/52
422/82.01
6,295,863 B1 * 10/2001 Ginder .................... G01M 3/04
403/27
9,080,926 B2 * 7/2015 Murray ................... G01M 13/04

FOREIGN PATENT DOCUMENTS

JP 2009257460 A 11/2009
WO 03100743 A2 12/2003

* cited by examiner

*Primary Examiner* — Thomas R. Hannon
(74) *Attorney, Agent, or Firm* — Bryan Peckjian; SKF USA Inc. Patent Dept.

(57) ABSTRACT

A bearing arrangement is provided having a bearing mounted in a housing, wherein a grease lubricant is present within the housing for lubricating the bearing. The arrangement further provides a support frame made of an electrically insulating material, arranged in a space within the housing between the bearing and a housing seal. The support frame is provided with at least one electrode pair having first and second electrodes arranged such that a portion of the grease lubricant is located between the first and second electrodes. A capacitance meter is provided for measuring a capacitance between the first and second electrodes. The first and second electrodes of the at least one electrode pair are provided on a radially oriented surface of the support frame, which surface is arranged such that the grease is able to move in an axial direction over the surface.

12 Claims, 3 Drawing Sheets

CAPACITANCE MEASUREMENT IN A BEARING HOUSING

CROSS REFERENCE TO RELATED APPLICATION

This is a Non-Provisional Patent Application, filed under the Paris Convention, claiming the benefit of Great Britain (GB) Patent Application Number 1505264.0, filed on 27 Mar. 2015, which is incorporated herein by reference in its entirety.

TECHNOLOGICAL FIELD

The present invention relates to a bearing arrangement comprising a bearing mounted in a housing, whereby the arrangement provides a capacitance sensor, which may be used, for example, to determine a degree of contamination in a grease lubricant that is present within the housing.

BACKGROUND OF THE INVENTION

To enable a long service life, it is important that a bearing is properly lubricated. Most bearings are grease lubricated, whereby oil from the grease generates an oil film during bearing operation, which separates the rolling contact surfaces. If the oil film breaks down, metal-to-metal contact occurs that can quickly lead to bearing failure if the oil film is not replenished. Monitoring methods are therefore applied in some applications to monitor the lubrication condition in a bearing, so that re-lubrication can be carried out before failure occurs. In EP1676041, for example, capacitance measurements are used to determine the film thickness of the oil film.

Lubricant contamination can also lead to early bearing failure. If an oil or grease lubricant contains abrasive particles, the rolling contact surfaces are likely to get damaged. The presence of water is also undesirable, as this can lead to corrosion. It is also possible for hydrogen embrittlement to occur due to the extreme contact pressures, which can be as high as 1 to 3 GPa, whereby water can break down into its constituent atoms causing hydrogen to penetrate the surface of the bearing elements, causing the surface to become more brittle. Water can also accelerate chemical degradation of a lubricating oil or of the thickener structure within a grease.

Therefore, in applications where a bearing might be exposed to the ingress of contamination, condition monitoring of the lubricant is sometimes applied.

Capacitance measurement can be used to detect contamination. JP 2007198576, for example, discloses a sealed bearing, whereby a pair of electrodes is provided on an inner, axially oriented surface of a seal, for detecting the ingress of water.

There is still room for improvement.

SUMMARY OF THE INVENTION

The present invention resides in bearing arrangement comprising a bearing mounted in a housing, whereby a grease lubricant is present within the housing for lubricating the bearing. The arrangement further provides a support frame, which is at least partly made of an electrically insulating material and is arranged in a space within the housing, so as to lie axially between the bearing and a housing seal. The support frame is provided with at least one electrode pair having first and second electrodes arranged such that a portion of the grease lubricant is located between the first and second electrodes. A capacitance meter is provided for measuring a capacitance between the first and second electrodes. The first and second electrodes of the at least one electrode pair are provided on a radially oriented surface of the support frame, which surface is arranged such that the grease is able to move in an axial direction over the surface.

In one example, the support frame is a ring or ring segment that is mounted to the housing. The support frame may thus have a simple construction that is easy to retro-fit to an existing bearing arrangement.

The first and second electrodes are provided on a radially inner surface of the ring or ring segment. Suitably, the ring or ring segment has a low radial height, such that a substantial radial gap exists between the ring (segment) and a shaft that is supported within the housing by the bearing. As a result, the grease in the bearing arrangement is not blocked from moving in an axial direction. This is beneficial in terms of enabling used grease to exit the bearing housing when fresh grease is added. Furthermore, grease can easily pass over the first and second electrodes, thereby enabling the electrodes to be cleaned by the grease. As a result, the capacitance that is measured after a re-lubrication event will accurately reflect the degree of contamination in the grease. If the electrodes were placed on an axially oriented surface of the support fame, there is a risk that used grease would get stuck there.

In one example, the first and second electrodes of the at least one electrode pair are circumferentially spaced from each other. Alternatively, the first and second electrodes may be arranged side-by-side in axial direction.

In a further example, the support frame provides first and second concentrically arranged rings or ring segments, such that a radial gap exists therebetween for allowing the passage of grease. Suitably, the first and second electrodes of the at least one electrode pair are provided on the first and second rings or ring segments respectively so as to be radially opposite each other.

In a further development of the invention, the support frame is provided with multiple electrode pairs. Using a ring segment as an example, the radially inner surface may be provided with a first electrode pair with circumferentially spaced electrodes and a second electrode pair with axially spaced electrodes. When the support frame provides concentric ring segments, a third electrode pair may have radially spaced electrodes.

The benefit of multiple electrode pairs is that it becomes possible to determine a spatial distribution of contamination levels within the housing, based on the relative location of each electrode pair and on the capacitance measured between each electrode pair. Localized areas of contamination can therefore be detected when e.g. a first capacitance measured between the first electrode pair is higher than a second capacitance measured between the second electrode pair.

Advantageously, the bearing arrangement may be provided with a second support frame with at least one electrode pair provided on a radially oriented surface. Suitably, the first and second support frames are arranged at either axial side of the bearing.

Since the capacitance of the lubricant depends on the composition of the lubricant, any change in composition resulting in different dielectric properties of the lubricant leads to a change in capacitance. In particular, the dielectric constant of water is considerably higher than the dielectric constant of conventionally used bearing lubricants such as oil and grease. The presence of metal particles in the lubricant will also change its dielectric constant. The measured capacitance can also indicate a degree of humidity within the bearing housing.

During normal operation of the bearing, no significant change in capacitance is expected. A sudden increase in capacitance can indicate the ingress of water or the presence of wear debris. A sudden decrease in capacitance could be indicative of grease leakage due to seal failure.

Consequently, if a severe change in capacitance is measured, a signal can be sent to e.g. a grease pump to initiate bearing re-lubrication, before damage to the bearing occurs.

In one embodiment of the invention, the bearing arrangement further provides a temperature sensor configured to determine the temperature of the grease, which may vary significantly during bearing operation. In particular, a temperature difference can be expected when comparing a static bearing with a bearing rotating at high speed. In general, the dielectric constant of grease does not vary significantly with temperature. The dielectric constant of water, however, does vary greatly with temperature. Therefore, by measuring the temperature, a small change in capacitance which might be interpreted as small change in water content of the grease, may instead be correctly attributed to a varying temperature. Moreover, by observing the temperature-dependent capacitance, the actual water content in the grease may be more accurately determined. The temperature sensor may be any type of temperature sensor known by the skilled person.

In one embodiment, the capacitance meter provides a processor that is programmed with upper and lower threshold values for the measured capacitance. The threshold values may be determined on the basis of previous measurements on a similar bearing arrangement that is lubricated with the same grease, or may be based on theoretical calculations. Alternatively or additionally, the processor may be configured to measure capacitance at a series of time intervals and to record the difference in capacitance values between consecutive measurements in the series. A threshold value for a maximum allowable difference may be defined, which is determined, for example, on the basis of calibration measurements. The measured difference is then compared with this threshold value, to determine if the condition of the grease lubricant has been adversely affected.

Advantageously, the processer is configured to transmit a signal to a lubrication pump in the event that a threshold is exceeded, for triggering a re-lubrication action. The bearing can thus be protected from operating in conditions of poor lubrication that could damage the bearing.

Other advantages of the invention will become apparent from the following detailed description and accompanying drawings.

DETAILED DESCRIPTION OF THE INVENTION

In the present detailed description, various embodiments of a bearing arrangement according to the present invention are discussed with reference to a spherical roller bearing. It should be noted that this by no means limits the scope of the present invention, which is equally applicable to any type of bearing that is mounted in a housing and is lubricated with grease.

Figure 1:
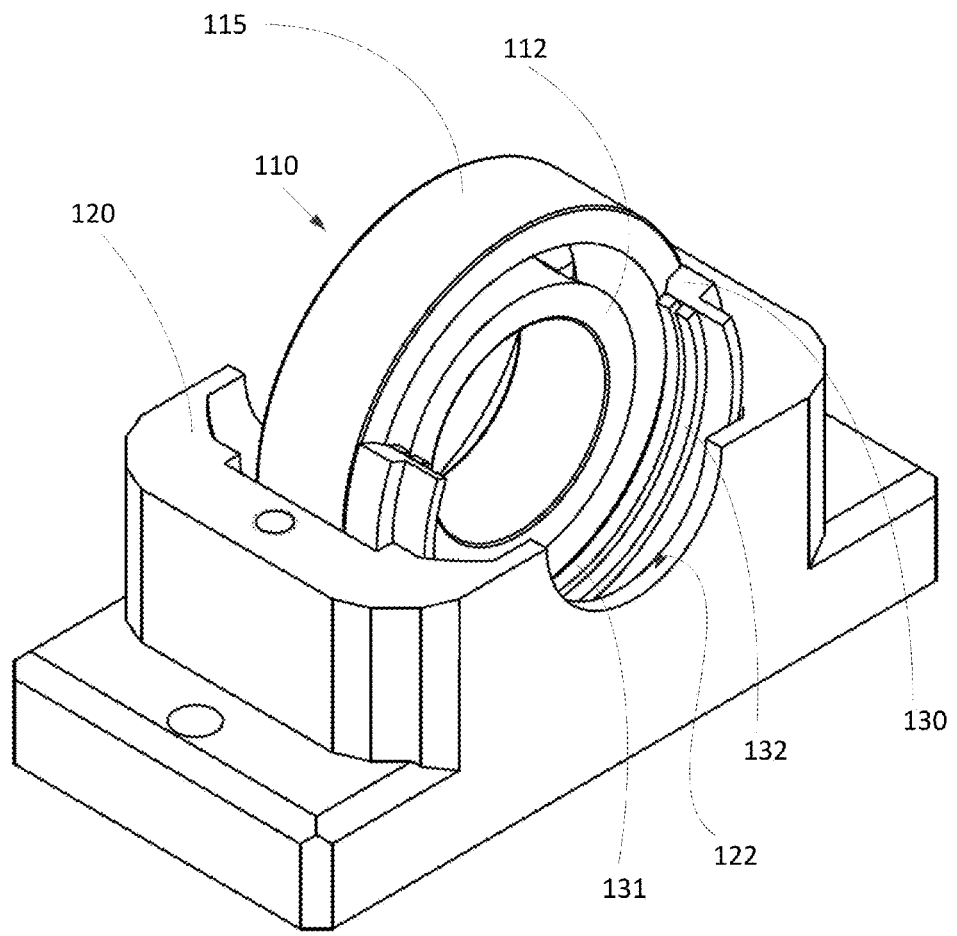
FIG. 1 shows a perspective view of parts of a bearing arrangement according to an embodiment of the invention, the arrangement comprising a first example of a support frame with conductive electrodes.

FIG. 1 shows an embodiment of a bearing arrangement 100 according to the invention, comprising a spherical roller bearing 110 that is mounted in a housing 120. An upper half of the housing has been removed from the drawing, to better reveal the component parts of the inventive bearing arrangement.

The bearing 110 provides an inner ring 112, an outer ring 115 and a number of spherical rollers (not shown) disposed between an inner raceway on the inner ring 112 and an outer raceway on the outer ring 115. In use, the bearing rotationally supports a shaft (not shown) relative to the housing 120. Typically, a radial seal is provided between a bore 122 of the housing and the shaft, for preventing the ingress of contaminants into the housing and for retaining a grease lubricant (not shown) within the housing.

In applications where the bearing operates in a highly contaminated environment, it is not always possible to prevent the ingress of contaminants, such as moisture. To ensure that the contamination does not reach a level that would seriously affect the lubricating ability of the grease or damage the bearing, the bearing arrangement 100 is provided with a capacitance sensor.

The capacitance sensor provides a support frame 130 made from an electrically insulating material e.g. a polymer material. In the depicted embodiment, the support frame is a ring segment that is essentially C-shaped. The support frame provides one electrode pair, consisting of first and second electrically conductive electrodes 131, 132. In the depicted example, the first and second electrodes are executed as arcuate strips, made of electrically conductive material, which are axially spaced relative to each other. The capacitance sensor further provides a capacitance meter (not shown) to which the first and second electrodes are connected.

The capacitance measured between the first and second electrodes depends on the dielectric constant of a dielectric material present between the electrodes. When grease is the dielectric, its dielectric constant changes if the grease contains moisture or e.g. metal particles. Measuring capacitance therefore provides an indication of the degree of contamination in the grease. If the measured amount exceeds a predefined threshold, an alarm is activated. Suitably, the alarm triggers a re-lubrication event, which may be performed manually by a maintenance technician or, if the bearing arrangement is connected to a lubrication pump, the alarm causes the lubrication pump to automatically deliver a prescribed amount of grease to the bearing arrangement 100.

Typically, the upper part of the bearing housing 120 provides a grease nipple for delivering fresh grease into the bearing arrangement. As the fresh grease is delivered, the used grease is forced out of the bearing arrangement, either through the seals, or an exit hole in a lower part of the housing 120, or a combination of both. It is therefore important that the capacitance sensor does not obstruct the flow of grease within the bearing housing.

According to the invention, the first and second electrodes 131, 132 are provided on a radially oriented surface of the support frame, i.e. on a radially inner surface of the ring segment. The ring segment 130 is disposed in a lower part of the housing, such that grease which accumulates in the lower housing part will be in contact with the electrodes.

Furthermore, the ring segment has a radial height that is significantly less than a radial gap between the shaft and inner surfaces of the housing. Therefore, grease is able to move in an axial direction, over the electrodes 131, 132 on the ring segment 130. This is beneficial not only in terms of enabling the movement of grease within the housing, but also in terms "cleaning" the electrodes, to enable more accurate determination of the contamination levels.

Figure 2:
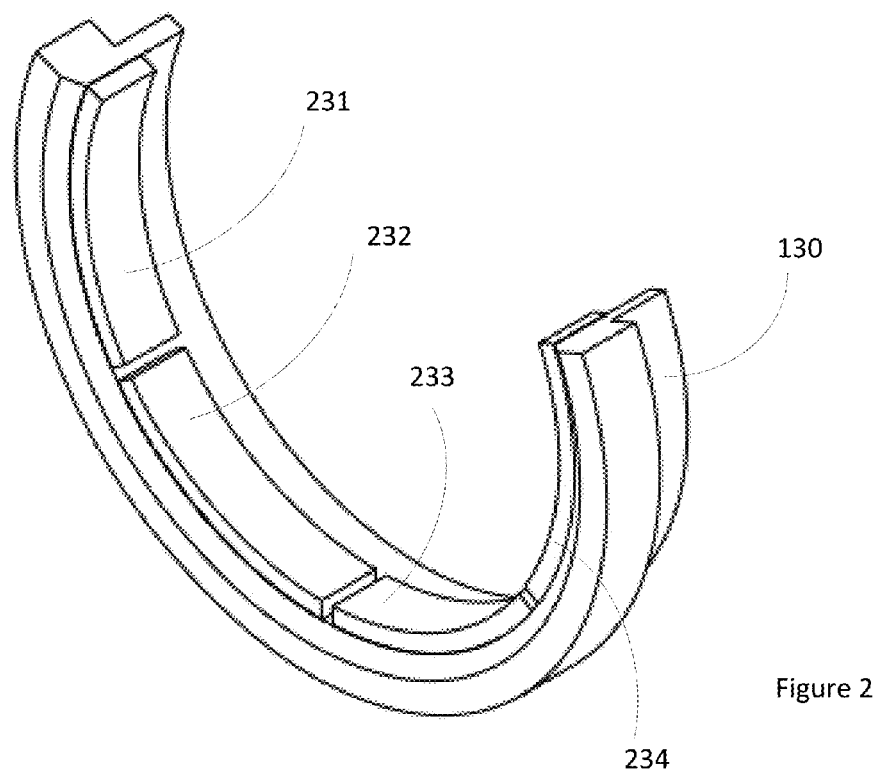
FIG. 2 shows a perspective view of a second example of a support frame with conductive electrodes.

In a further development of the invention, the capacitance sensor provides a support frame with a plurality of electrode pairs. A first example of the further development is shown in FIG. 2. The support frame is again a C-shaped ring segment 130, which is adapted for mounting in the lower part of a housing in a bearing arrangement such as shown in FIG. 1. A radially inner surface of the ring segment 130 is provided with four circumferentially spaced electrodes 231, 232, 233, 234, executed as arcuate strips. Circumferentially adjacent electrodes 231, 232 form the first and second electrodes of a first electrode pair; while circumferentially adjacent electrodes 233, 234 form the first and second electrodes of a second electrode pair. Each electrode pair is connected to the capacitance meter, which thus measures a first capacitance of the grease located between the electrodes 231, 232 of the first electrode pair and measures a second capacitance of the grease located between the electrodes 233, 234 of the second electrode pair.

The use of multiple electrode pairs enables localized areas of contamination to be identified. In embodiments where the bulk capacitance of the grease is measured, there is a risk that the measured value will indicate that the grease is in an acceptable condition, despite containing an area of localized contamination. This contaminated portion of grease might reach the bearing. Therefore, the capacitance meter is preferably configured to trigger a re-lubrication action if either of the first or second measured capacitance exceeds the predefined threshold.

Figure 3:
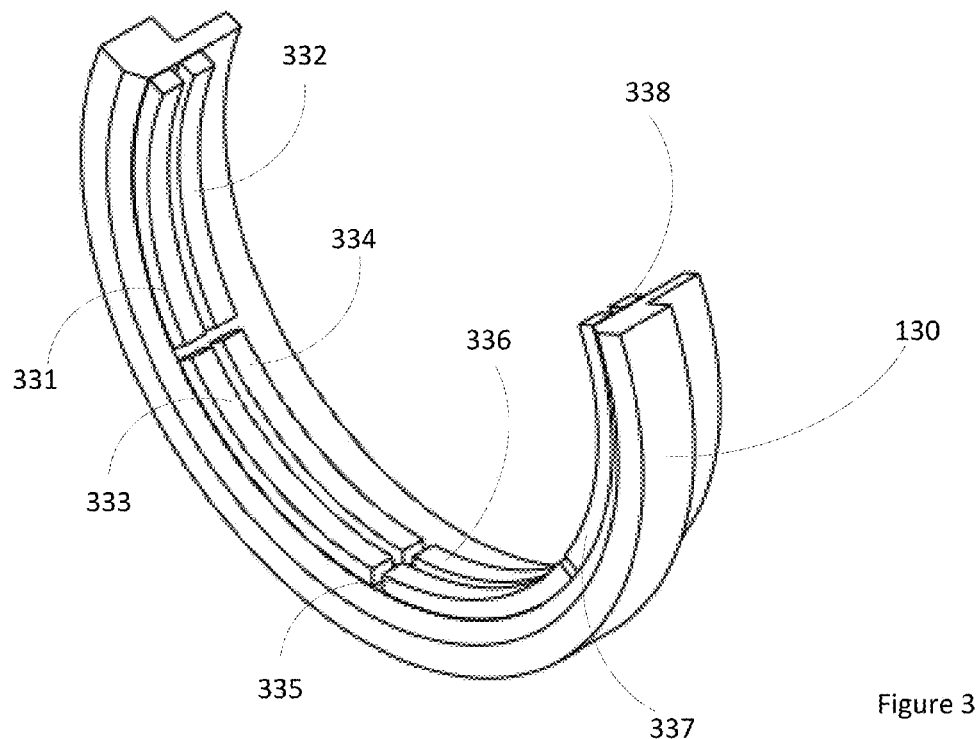
FIG. 3 shows a perspective view of a third example of a support frame with conductive electrodes.

A further example of a support frame with multiple electrode pairs is depicted in FIG. 3. The support frame is once again a ring segment 130, whereby a radially inner surface of the ring segment is provided with eight electrodes, executed as arcuate strips of electrically conductive material. A first set of four circumferentially spaced electrodes 331, 333, 335, 337 is axially spaced relative to a second set of four circumferentially spaced electrodes 332, 334, 336, 338. An electrode pair may be formed by any two electrodes. In one embodiment, each electrode pair is formed by axially adjacent electrodes e.g. 331 and 332. In other embodiment each electrode pair is formed by circumferentially adjacent electrodes, e.g. 332 and 334. A combination of axially spaced and circumferentially spaced electrode pairs is also possible. Each electrode is connected to the capacitance meter, which measures the capacitance of the grease that is located between each electrode pair. It is thus possible to measure capacitance in axial direction and/or circumferential direction at multiple locations within the housing, to more accurately detect areas of localized contamination within the grease lubricant.

Figure 4:
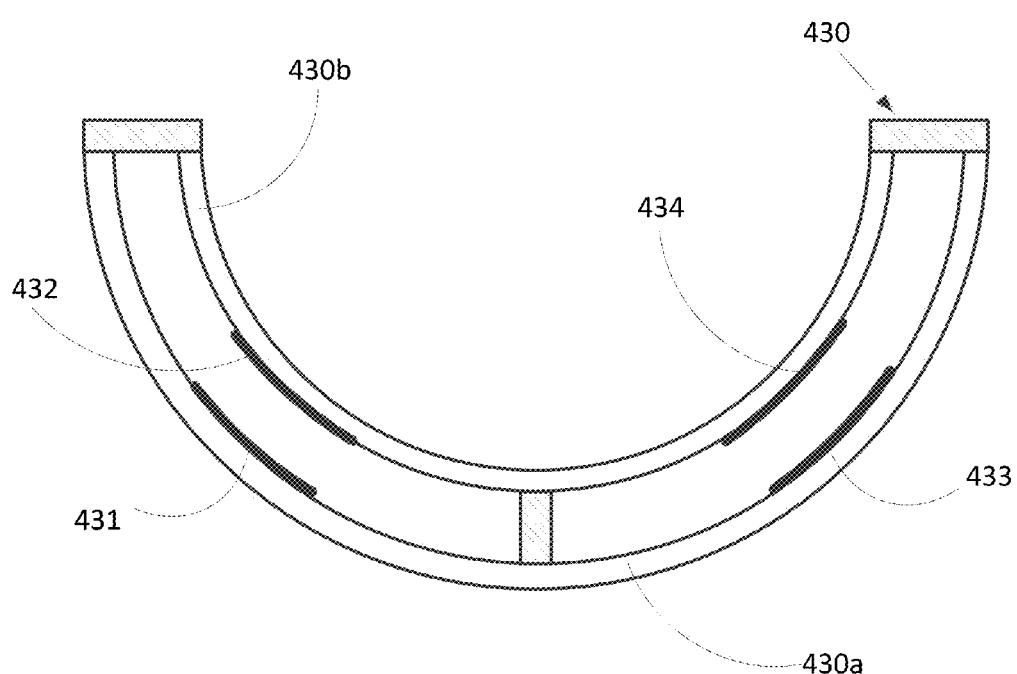
FIG. 4 shows a side view of a fourth example of a support frame with conductive electrodes.

A still further example of a support frame with multiple electrode pairs is depicted in FIG. 4. The support frame is made of an electrically insulating material and provides a first ring segment, adapted for mounting to the lower part of a bearing housing. The support frame further provides a second ring segment 430b, concentrically arranged relative to the first ring segment 430a, whereby a radial gap exists between the segments. The radial gap allows grease to move in an axial direction between the ring segments. For measuring capacitance in a radial direction, at two locations, a first electrode pair comprising radially opposite first and second electrodes 431, 432 and a second electrode pair comprising radially opposite first and second electrodes 433, 434 are provided on the support frame 430. In accordance with the invention, the first electrodes 431, 433 of the first and second pair are provided on a radially outer surface of the first ring segment 430a; the second electrodes 432, 434 of the first and second pair are provided on a radially inner surface of the second ring segment 430b.

In a further embodiment, a support frame such as depicted in FIG. 4 is provided with at least one electrode pair having radially spaced first and second electrodes and is further provided with at least one electrode pair having axially spaced first and second electrodes and at least one electrode pair having circumferentially spaced first and second electrodes. The capacitance of the grease can thus be measured in radial direction, in axial direction and in circumferential direction, enabling an accurate determination of the spatial distribution of contamination within the grease lubricant.

A number of aspects/embodiments of the invention have been described. It is to be understood that each aspect/embodiment may be combined with any other aspect/embodiment. Moreover the invention is not restricted to the described embodiments, but may be varied within the scope of the accompanying patent claims.

The invention claimed is:

1. A bearing arrangement comprising:
a bearing mounted in a housing, the bearing having an inner ring an outer ring and a plurality of rolling elements arranged between the inner and outer rings;
a grease lubricant provided within the housing to lubricate the bearing;
a support frame arranged in a space within the housing between the bearing and a housing seal, the support frame being provided with at least one electrode pair having first and second electrodes that are arranged such that a portion of the grease lubricant is located between the first and second electrodes; and
a capacitance meter configured to measure a capacitance between the first and second electrodes, wherein
the first and second electrodes of the at least one electrode pair are provided on a radially oriented surface of the support frame.

2. The bearing arrangement according to claim 1, wherein the support frame provides at least one of a ring and ring segment with a radial height that is substantially smaller than a radial gap between an inner surface of the housing and a shaft that is supported in the housing by the bearing.

3. The bearing arrangement according to claim 2, wherein the at least one of the ring and ring segment is mounted in a lower part of the housing.

4. The bearing arrangement according to claim 2, wherein the support frame provides first and second concentrically arranged rings or ring segments, wherein a radial gap exists between the rings or ring segments for allowing the passage of grease, and wherein the first and second electrodes of at least one electrode pair are respectively provided on radially opposite surfaces of the first and second rings or ring segments.

5. The bearing arrangement according to claim 4, wherein the support frame further comprises at least a second electrode pair having at least one of a circumferentially and axially spaced first and second electrodes.

6. The bearing arrangement according claim 1, wherein the first and second electrodes of at least one electrode pair are axially spaced from each other.

7. The bearing arrangement according to claim 1, wherein the first and second electrodes of at least one electrode pair are circumferentially spaced from each other.

8. The bearing arrangement according to claim 1, wherein the support frame provides a plurality of electrode pairs, wherein each electrode pair has first and second electrodes that are connected to the capacitance meter, and wherein the capacitance meter is configured to measure the capacitance between each electrode pair.

9. The bearing arrangement according to claim 8, wherein the support frame provides at least one electrode pair having circumferentially spaced first and second electrodes, and at least one electrode pair having axially spaced first and second electrodes.

10. The bearing arrangement according claim 1, further comprising a grease pump in combination with the bearing arrangement, the pump being configured to deliver a prescribed volume of grease to the bearing arrangement when a capacitance value is measured between an electrode pair that exceeds a predefined threshold.

11. The bearing arrangement according to claim 1, further comprising first and second support frames, wherein each frame is provided with at least one electrode pair for measuring capacitance.

12. The bearing arrangement according to claim 11, wherein the first support frame is arranged at a first axial side of the bearing and the second support frame is arranged at a second axial side of the bearing.

* * * * *